(12) United States Patent
Hagadorn et al.

(10) Patent No.: US 8,519,147 B2
(45) Date of Patent: Aug. 27, 2013

(54) CARBENE COMPLEXES OF LITHIUM AND/OR MAGNESIUM METAL SALTS, AND USES THEREOF

(75) Inventors: John R. Hagadorn, Houston, TX (US); Matthew W. Holtcamp, Huffman, TX (US); Matthew S. Bedoya, Humble, TX (US); Renuka N. Ganesh, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 107 days.

(21) Appl. No.: 12/939,063

(22) Filed: Nov. 3, 2010

(65) Prior Publication Data
US 2011/0112304 A1 May 12, 2011

Related U.S. Application Data

(60) Provisional application No. 61/259,521, filed on Nov. 9, 2009, provisional application No. 61/259,514, filed on Nov. 9, 2009.

(51) Int. Cl.
*C07F 3/02* (2006.01)
*C07F 1/02* (2006.01)

(52) U.S. Cl.
USPC ........................................ 548/103; 548/403

(58) Field of Classification Search
USPC ................................. 548/103, 403
See application file for complete search history.

(56) References Cited

U.S. PATENT DOCUMENTS

| 4,545,941 | A | 10/1985 | Rosenburg |
| 6,900,347 | B2 | 5/2005 | Paulson et al. |
| 7,119,216 | B2 | 10/2006 | Newman et al. |
| 7,205,424 | B2 | 4/2007 | Nolan |
| 7,268,242 | B2 | 9/2007 | Pederson et al. |
| 7,312,331 | B2 | 12/2007 | Bertrand et al. |
| 7,632,772 | B2 | 12/2009 | Zhan |
| 2005/0070750 | A1 | 3/2005 | Newman et al. |
| 2006/0287450 | A1 | 12/2006 | Kohler et al. |
| 2007/0043180 | A1 | 2/2007 | Zhan |
| 2007/0270621 | A1 | 11/2007 | Millis et al. |
| 2008/0027194 | A1 | 1/2008 | Schrodi |
| 2008/0064891 | A1 | 3/2008 | Lee |
| 2008/0269525 | A1 | 10/2008 | Bertrand et al. |
| 2009/0048459 | A1 | 2/2009 | Tupy et al. |
| 2009/0069516 | A1 | 3/2009 | Obrecht et al. |
| 2009/0187035 | A1 | 7/2009 | Ko et al. |
| 2009/0259065 | A1 | 10/2009 | Abraham et al. |
| 2010/0022789 | A1 | 1/2010 | Mignani et al. |

FOREIGN PATENT DOCUMENTS

| EP | 2 151 446 | 2/2010 |
| JP | 58-154594 | 9/1983 |
| WO | WO 00/71554 | 11/2000 |
| WO | WO 2004/062763 | 7/2004 |
| WO | WO 2006/138166 | 12/2006 |
| WO | WO 2008/010961 | 1/2008 |
| WO | WO 2008/046106 | 4/2008 |
| WO | WO 2008/095785 | 8/2008 |
| WO | WO 2008/125568 | 10/2008 |
| WO | WO 2008/140468 | 11/2008 |
| WO | WO 2009/009597 | 1/2009 |
| WO | WO 2009/126831 | 10/2009 |

OTHER PUBLICATIONS

Arnold et al., "*Asymmetric Lithium(I) and Copper (II) Alkoxy-N-Heterocyclic Carbene Complexes; Crystallographic Charaterisation and Lewis Acid Catalysis*", Chemical Communications, 2004, pp. 1612-1613.
Arnold et al., "*Anionic Amido N-Heterocyclic Carbenes; Synthesis of Covalently Tethered Lanthanide-Carbene Complexes*", Angewandte Chemie International Edition, 2003, vol. 42, pp. 5981-5984.
De Fremont et al., "*Cationic NHC-Gold(I) Complexes: Synthesis, Isolation and Catalytic Activity*", Journal of Organometallic Chemistry, 2009, vol. 694, pp. 551-560.
Frankel et al., "*A Homopletic Carbene-Lithium Complex*", Angewandte Chemie International Edition, 2001, vol. 40, No. 10, pp. 1907-1910.
Hahn et al., "*Heterocyclic Carbenes: Synthesis and Coordination Chemistry*", Angewandte Chemie International Edition, 2008, vol. 47, pp. 3122-3172.
Herrmann et al., "*N-Heterocyclic Carbenes[+] : Generation under Mild Conditions and Formation of Groups 8-10 Transition Metal Complexes Relevant to Catalysts*", Chemistry, A European Journal, 1996, vol. 2, No. 7, pp. 772-780.
Allen et al., "*Well-Defined Silica-Supported Olefin Metathesis Catalysts*", Organic Letters, 2009, vol. 11, No. 6, pp. 1261-1264.
Blum et al., "*Synthesis of N-Heterocyclic Carbene-Containing Metal Complexes from 2-(Pentafluorophenyl)Imidazolidines*", Organometallics, 2007, vol. 26, No. 8, pp. 2122-2124.
Chung et al., "*Olefin Metathesis Catalyst: Stabilization Effect of Backbone Substitutions of N-Heterocyclic Carbene*", Organic Letters, 2008, vol. 10, No. 13, pp. 2693-2696.
Dinger et al., "*Adamantyl-Substituted N-Heterocyclic Carbene Ligands in Second-Generation Grubbs-Type Metathesis Catalysts*", Organometallics, 2003, vol. 22, No. 25, pp. 5291-5296.

(Continued)

*Primary Examiner* — Shawquia Young
(74) *Attorney, Agent, or Firm* — Catherine L. Bell

(57) ABSTRACT

This invention relates to a carbene complex of metal salt represented by the formula:

$$[T-M(R)_c]_n$$

wherein, R is a monoanionic group; c is 1 or 2; M is a Li or Mg; T is a cyclic carbene ligand; and n is selected from the group of integers comprising 1 to 24 wherein the complex has 50% or less decomposition when stored in 0.01 molar benzene at 23° C. for a period of 1 hour. This invention also relates to transition-metal-carbene complexes prepared from such carbene complexes of metal salts, where the transition-metal-carbene complex is represented by the formula: $[M^*(T)(L^0)_q(L^{1-})_s(L^{2-})_t]^g$, where $M^*$ is a transition metal from Group 6, 7, 8, 9, 10, 11 or 12, T is a cyclic carbene ligand, $L^0$ is a neutral ligand, $L^{1-}$ is a monoanionic ligand, $L^{2-}$ is a dianionic ligand, q is 0, 1, 2, 3 or 4, s is 0, 1, 2, 3, or 4, t is 0, 1, 2, 3, or 4, g is the overall charge of the molecule. The transition-metal-carbene complexes may be used for synthesis reactions, including metathesis of olefins.

14 Claims, 1 Drawing Sheet

(56) References Cited

OTHER PUBLICATIONS

Ledoux et al., "*Comparative Investigation of Hoveyda-Grubbs Catalysts Bearing Modified N-Heterocyclic Carbene Ligands*", Advanced Synthesis & Catalysis, 2007, vol. 349, No. 10, pp. 1692-1700.

Ledoux et al., "*N-N'Dialkyl- and N-Alkyl-N-Mesityl-Substituted N-Heterocyclic Carbenes as Ligands in Grubbs Catalysis*", Chemistry, A European Journal, 2006, vol. 12, No. 17, pp. 4654-4661.

Leuthaußer et al., "*π-Face Donor Properties of N-Heterocyclic Carbenes in Grubbs II Complexes*", Chemistry, A European Journal, 2008, vol. 14, No. 18, pp. 5465-5481.

Lichtenheldt et al., "*Alternating Ring-Opening Metathesis Copolymerization by Grubbs-Type Initiators with Unsymmetrical N-Heterocyclic Carbenes*", Chemistry, A European Journal, 2009, vol. 15, No. 37, pp. 9451-9457.

Santhosh Kumar et al., "*Factors Relevant for the Regioselective Cyclopolymerization of 1,6-Heptadiynes, N,N-Dipropargylamines, N,N-Dipropargylammonium Salts, and Dipropargyl Ethers by RuIV-Alklidene-Based Metathesis Initiators*", Journal of the American Chemical Society, 2009, vol. 131, No. 1, pp. 387-395.

Sußner et al., "*π-Face Donor Properties of N-Heterocyclic Carbenes*", Chemical Communications, 2005, No. 43, pp. 5417-5419.

Tiede et al., "*Highly Active Chiral Ruthenium-based Metathesis Catalysts Through a Monosubstitution in the N-Heterocyclic Carbene*", Angewandte Chemie, International Edition, 2010, vol. 49, No. 23, pp. 3972-3975.

Vehlow et al., "*Alternating Copolymerizations Using a Grubbs-Type Initiator with an Unsymmetrical, Chiral N-Heterocyclic Carbene Ligand*", Angewandte Chemie, International Edition, 2008, vol. 47, No. 14, pp. 2615-2618.

Vehlow et al., "*Deactivation of Ruthenium Olefin Metathesis Catalysts Through Intromolecular Carbene-Arene Bond Formation*", Angewandte Chemie, International Edition, 2007, vol. 46, No. 42, pp. 8082-8085.

Vougioukalakis et al., "*Ruthenium-Based Olefin Metathesis Catalysts Coordinated with Unsymmetrical N-Heterocyclic Carbene Ligands: Synthesis, Structure, and Catalytic Activity*", Chemistry, A European Journal, 2008, vol. 14, No. 25, pp. 7545-7556.

Vougioukalakis et al., "*Ruthenium Olefin Metathesis Catalysts Bearing an N-Fluorophenyl-N-Mesityl-Substituted Unsymmetrical N-Heterocyclic Carbene*", Organometallics, 2007, vol. 26, No. 9, pp. 2469-2472.

Xu et al., "*Development of Building Blocks for the Synthesis of N-Heterocyclic Carbene Ligands*", Organic Letters, 2005, vol. 7, No. 21, pp. 4605-4608.

Alder et al., "*Complexation of Stable Carbenes With Alkali Metals*", Chemical Communications, 1999, No. 3, pp. 241-242.

Anderson et al., "*Synthesis and Reactivity of Olefin Metathesis Catalysts Bearing Cyclic (Alkyl)(Amino)Carbenes*", Angewandte Chemie, International Edition, 2007, vol. 46, No. 38, pp. 7262-7265.

Anderson et al., "*Kinetic Selectivity of Olefin Metathesis Catalysts Bearing Cyclic (Alkyl)(Aminoi)Carbenes*", Organometallics, 2008, vol. 27, No. 4, pp. 563-566.

Arduengo III et al., "*Carbene-Lithium Interactions*", Chemistry Letters, 1999, vol. 28, No. 10, pp. 1021-1022.

Arduengo et al., "*Carbene Adducts of Magnesium and Zinc*", Journal of Organometallic Chemistry, 1993, vol. 462, No. 1-2, pp. 13-18.

Arduengo et al., *Adducts of Carbenes with Group II and XII Metallocenes*, Organometallics, 1998, vol. 17, No. 15, pp. 3375-3382.

Arnold et al., "*Magnesium and Zinc Complexes of Functionalised, Saturated N-heterocyclic Carbene Ligands: Carbene lability and Functionalisation, and Lactide Polymerisation Catalysis*", Journal of Chemical Society, Dalton Transactions, 2009, No. 35, pp. 7236-7247.

Arrowsmith et al., "*AHydride-Rich Magnesium Cluster*", Angewandte Chemie, International Edition, 2009, vol. 48, No. 22, pp. 4013-4016.

Azizoglu et al., "*Substituent Effects on the Ring-Opening Mechanism of Lithium Bromocyclopropylidenoids to Allenes*", Journal of Organic Chemistry, 2008, vol. 73, No. 21, pp. 8182-8188.

Berthelot et al., "*Gas-Phase Reactivity of (C5H5Mg)+ Complexes: An Experimental and Theoretical Study*", Journal of Physical Chemistry. A molecules, Spectroscopy, Kinetics, Enironment and General Theory, 1998, vol. 102, No. 29, pp. 6025-6034.

Bourisson et al., "*Stable Carbenes*", Chemical Reviews, 2000, vol. 100, No. 1, pp. 39-91.

Burdett et al., "*Renewable Monomer Feedstocks via Olefin Metathesis: Fundamental Mechanistic Studies of Methyl Oleate Ethenolysis with the First-Generation Grubbs Catalyst*", Organometallics, 2004, vol. 23, No. 9, pp. 2027-2047.

Diez-Gonzalez et al., "*N-Heterocyclic Carbenes in Late Transition Metal Catalysis*", Chemical Reviews, 2009, vol. 109, No. 8, pp. 3612-3676.

Dragutan et al., "*Ruthenium Indenylidene Complexes: Metathesis Catalysts With Enhanced Activity*", Platinum Metals Rev. 2005, vol. 49, Issue 1, p. 33-40.

Furstner et al., "*Ruthenium Carbene Complexes with N,N'-Bis(mesityl)imidazol-2-ylidene Ligands: RCM Catalysts of Extended Scope*", J. Org. Chem., 2000, vol. 65, Issue 7, pp. 2204-2207.

Grant No. DE-FG36-04GO14016, "*Platform Chemicals from an Oilseed Biorefinery*," awarded by the Department of Energy, Final Technical Report, Nov. 30, 2006.

Hermann et al., "*Heterocyclic Carbenes: A High-Yielding Synthesis of Novel, Functionalized N-Heterocyclic Carbenes in Liquid Ammonia*", Chemistry, A European Journal, 1996, vol. 2, No. 12, pp. 1627-1636.

Hoveyda et al., "*A Recyclable Ru-Based Metathesis Catalyst*", Journal of American Chemical Society, 1999, vol. 121, pp. 791-799.

Kingsbury et al., "*A Recyclable Ru-Based Metathesis Catalyst*", J. Am. Chem. Soc., 1999, vol. 121, pp. 791-799.

Jazzar et al., "*A New Synthetic Method for the Preparation of Protonated-NHCs and Related Compounds*", Journal of Organometallic Chemistry, 2006, vol. 691, No. 14, pp. 3201-3205.

Jazzar et al., "*Intramolecular "Hydroiminiumation" of Alkenes: Application to the Synthesis of Conjugate Acids of Cyclic Alkyl Amino Carbenes (CAACs)*", Angewandte Chemie, International Edition, 2007, vol. 46, No. 16, pp. 2899-2902.

Lavallo et al., "*A Rigid Cyclic (Alkyl)amino)carbine)Ligand Leads to Isolation of Low-Coordinate Transition-Metal Complexes*", Angew. Chem. Int. Ed., 2005, vol. 44, No. 44, pp. 7236-7239.

Lavallo et al., "*Isolation of Cyclopropenylidene-Lithium Adducts: The Weiss-Yoshida Reagent*", Angewandte Chemie, International Edition, 2006, vol. 45, No. 40, pp. 6652-6655.

Lavallo et al., "*Stable Cyclic (Alkyl)(Amino)Carbenes as Rigid or Flexible, Bulky, Electron-Rich Ligands for Transition-Metal Catalysts: A quaternary Carbon Atom Makes the Difference*", Angew. Chem. Int. Ed., 2005, vol. 44, No. 35, pp. 5705-5709.

Rybak et al., "*Metathesis a Versatile Tool in Olechemistry*", Eur. J. Lipid Sci. Technol, Weinheim, 2008, vol. 110, pp. 797-804.

Scholl et al., "*Synthesis and Activity of a new Generation of Ruthenium-Based Olefin Metathesis Catalysts Coordinated with 1,3-Diesityl-4, 5-Dihydroimidazol-2-ylidene Ligands*" Org. Letters, 1999, vol. 1, pp. 953-956.

Schrodi et al., "*Ruthenium Olefin Metathesis Catalysts for the Ethenolysis of Renewable Feedstocks*", Clean: Soil, Air, Water, vol. 36, Issue 8, pp. 669-673.

Schumann et al., "*Metallocenes of the Alkaline Earth Metals and Their Carbene Complexes*", Journal of Organometallic Chemistry, 2001, vol. 617-618, pp. 588-600.

Sigal et al., "*Are Disilacyclopropylidenes and Their Carbenoids Good Precursors for the Unknown 1, 3-Disilaallenes?*", Journal of Organometallic Chemistry, 2001, vol. 636, No. 1-2, pp. 148-156.

Stasch et al., "*Synthesis and Characterization of Alkynyl Complexes of Groups 1 and 2*", Chemistry, An Asian Journal, 2009, vol. 4, No. 9, pp. 1451-1457.

Tamm et al., "*Pentacarbonylchromium(0) and -tungsten(0) Complexes with the Bis(Diisopropylamino) Cyclopropenylidene Ligand*", Journal of Organometallic Chemistry, 1995, vol. 501, No. 1, pp. 309-313.

Vehlow et al., "*Ruthenium Metathesis Catalysts with Saturated Unsymmetrical N-Heterocyclic Carbene Ligands*", Organometallics, 2006, vol. 25, No. 1, pp. 25-28.

Assay, et al., "*Cyclic(amino)[bis(ylide)]carbene as an Anionic Bidentate Ligand for Transition-metal Complexes*", Inorg. Chem., 2008, vol. 47, pp. 3949-3951.

Huang et al., "*Kinetic and Thermodynamic Study of Syn-anti Isomerization of Nickel Complexes Bearing Aminio-linked N-heterocyclic Carbene Ligands: The Effect of the Pendant Arm of the NHC*", Organometallics, 2009, vol. 28, pp. 4316-4323.

Shih et al., "*Synthesis and Structure of an Amino-linked N-heterocyclic Carbene and the Reactivity of its Aluminum Adduct*", Organometallics, 2009, vol. 28, 1060-1067.

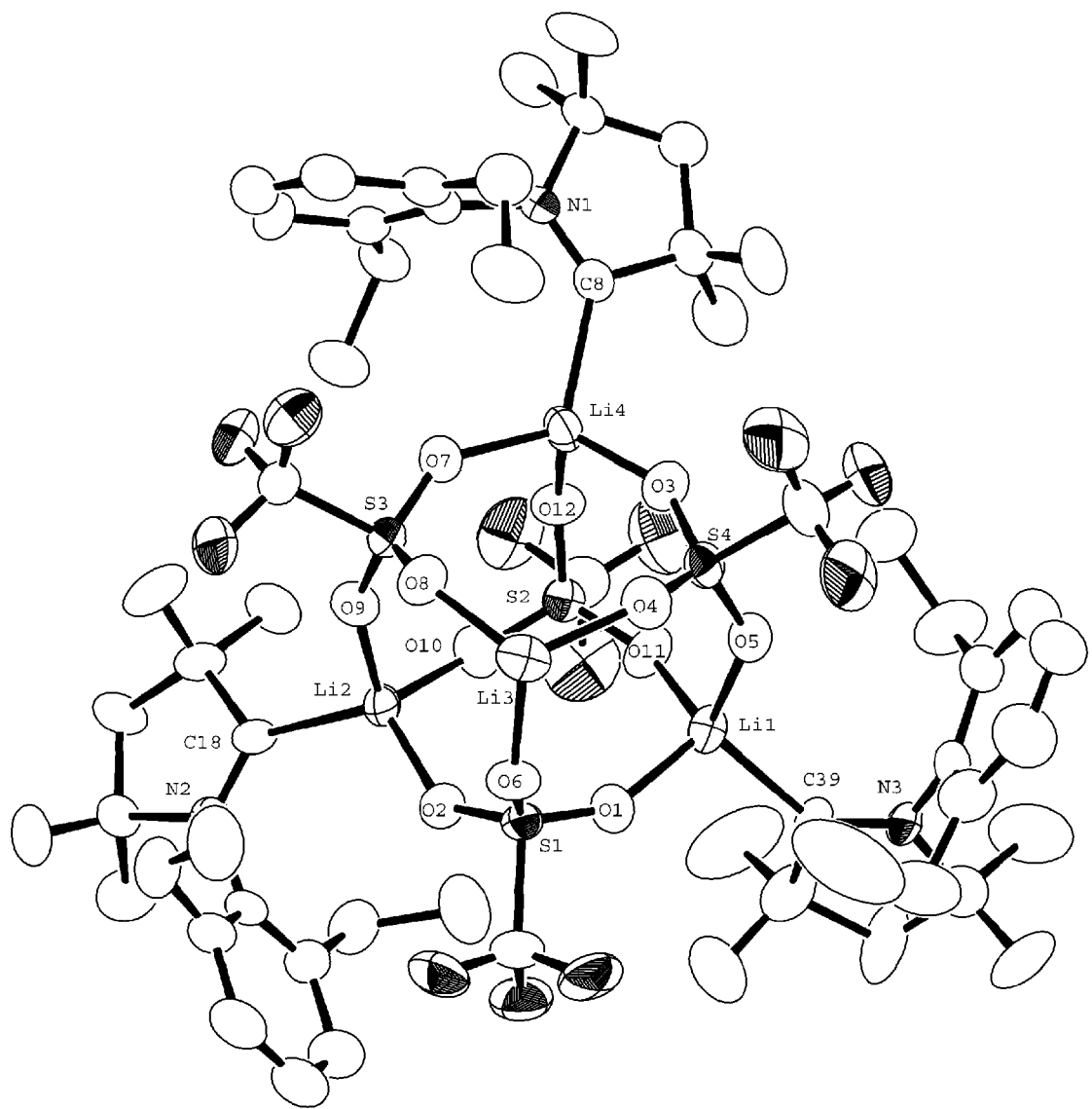
Molecular depiction of Compound 1

CARBENE COMPLEXES OF LITHIUM AND/OR MAGNESIUM METAL SALTS, AND USES THEREOF

PRIORITY CLAIM

This invention claims priority to and the benefit of U.S. Ser. No. 61/259,521, filed Nov. 9, 2009.

STATEMENT OF RELATED APPLICATIONS

This invention is also related to patent application U.S. Ser. No. 12/939,054 (issued as U.S. Pat. No. 8,063,232), filed Nov. 3, 2010 and claiming priority to and the benefit of U.S. Ser. No. 61/259,514, filed Nov. 9, 2009.

FIELD OF THE INVENTION

This invention generally relates to carbene complexes of lithium and/or magnesium metal salts and to methods of preparation thereof as well as uses of such salts in preparation of catalyst compositions.

BACKGROUND OF THE INVENTION

The development of catalysts with a diverse range of ligand frameworks to perform specific transformations has proven critical for both industry and academia. The success of both homogeneous and heterogeneous catalysis may be largely attributed to the use of various ligands to tune the behavior of transition-metal-containing catalyst complexes. Advances in the synthesis of transition-metal-containing complexes have in turn allowed for the development of novel industrial processes and the improvement of known processes in terms of scope, mildness and catalyst loadings.

For instance, transition metal complexes of cyclic alkyl amino carbenes have been found useful as catalysts for a range of applications (Bertrand et al., U.S. Pat. No. 7,312,331). Pd-cyclic alkyl amino carbenes complexes have been described by Bertrand and coworkers (*Angew. Chem. Int. Ed.* 2005, 44, 7236-7239) to be highly efficient catalysts for the alpha-arylation of ketones and aldehydes. Ru-cyclic alkyl amino carbenes complexes, which are have been used as catalysts for alkene metathesis processes, are also of great interest. In particular, a series of Ru-cyclic alkyl amino carbenes alkylidenes have been found to be highly active catalysts for the ethenolysis of methyl oleate as described in the Final Technical Report "Platform Chemicals from an Oilseed Biorefinery" (Award DE-FG36-04GO140016, Department of Energy funded joint project of Materia and Cargill).

Although this series of Ru-cyclic alkyl amino carbenes complexes demonstrates tremendous utility, the known synthetic routes to these Ru-cyclic alkyl amino carbenes alkylidenes are far from ideal, especially those routes to transition metal complexes of cyclic alkyl amino carbenes ligands having relatively small substituents such as 2,4,6-trimethylphenyl- or 2,6-diethylphenyl-bound to the nitrogen atom (*Angew. Chem. Int. Ed.* 2007, 46, 7262-7265). These synthetic routes usually include ligand substitution reactions which need to be conducted at sub-ambient temperatures. These reactions tend to be slow, typically resulting in poor yields and add to the cost of the synthetic route. Indeed, the desired Ru-cyclic alkyl amino carbenes complex is often obtained in poor yield. For example, although the above Final Technical Report identified complex 18 (shown in equation 5 of *Angew. Chem. Int. Ed.* 2007, 46, 7262-7265) as being the highest activity catalyst for methyl oleate ethenolysis, complex 18 was only obtained in an isolated yield of 18%. Accordingly, there is a need for improved synthetic routes to transition-metal-carbene complexes, in particular Ru-cyclic alkyl amino carbenes complexes, in order for these promising catalysts to be commercially viable.

The current invention relates to a carbene complex of a lithium and/or magnesium salt useful as a synthon in the preparation of transition-metal-carbene complexes. The current invention also relates to an improved synthetic route to transition-metal-carbene complexes by using a carbene complex of a lithium and/or magnesium salt as a synthon. More particularly, the present invention relates to an improved synthetic route to Ru-cyclic alkyl amino carbenes complexes using a carbene complex of a lithium and/or magnesium salt. Advantageously, this improved synthetic route may be carried at temperatures at or above ambient, removing the need for coolants and thereby reducing the overall cost of the synthetic route. Even more advantageously, the improved synthetic route using the invention described herein provides transition-metal-carbene complexes in significantly higher yields than previous reported. Accordingly, the present invention provides a facile, mild, high-yield route to transition-metal-carbene complexes.

SUMMARY OF THE INVENTION

This invention relates to a carbene complex of metal salt represented by the formula:

wherein, R is a monoanionic group; c is 1 or 2; M is a Li or Mg; T is a cyclic carbene ligand; and n is selected from the group of integers comprising 1 to 24 wherein the complex has 50% or less decomposition when stored in 0.01 molar benzene at 23° C. for a period of 1 hour.

This invention also relates to transition-metal-carbene complexes prepared from such carbene complexes of metal salts, where the transition-metal-carbene complex is preferably represented by the formula: $[M^*(T)(L^0)_q(L^{1-})_s(L^{2-})_t]^g$, where M* is a transition metal from Group 6, 7, 8, 9, 10, 11, or 12, T is a cyclic carbene ligand, $L^0$ is a neutral ligand, $L^{1-}$ is a monoanionic ligand, $L^{2-}$ is a dianionic ligand, q is 0, 1, 2, 3 or 4, s is 0, 1, 2, 3, or 4, t is 0, 1, 2, 3, or 4, and g is the overall charge of the complex. The transition-metal-carbene complexes may be used for synthesis reactions, including metathesis of olefins.

BRIEF DESCRIPTION OF THE FIGURES

FIG. 1 depicts the structure of the carbene-lithium salt adduct Compound 1 drawn with 30% thermal ellipsoids as determined by single-crystal X-ray diffraction. The carbene ligand coordinated to Li(3) and the hydrogen atoms are omitted for clarity.

DETAILED DESCRIPTION

This invention generally relates to carbene complexes of lithium and/or magnesium salts, more particularly, to cyclic alkyl amino carbene (CAAC) complexes of lithium and/or magnesium salts, and even more particularly, to methods of preparation of transition-metal-carbene complexes using carbene complexes of lithium and/or magnesium metal salts in improved yields as compared to conventional routes.

The present invention comprises a carbene complex comprising a lithium and/or magnesium salt. The present invention also relates to a novel synthetic route to transition-metalcarbene complexes, such as those useful for the cross-metathesis of olefins. More particularly, the present invention comprises a CAAC complex of a lithium and/or magnesium salt. Even more particularly, the present invention comprises the use of a CAAC complex of a lithium and/or magnesium salt to prepare a transition-metal-carbene complex.

For purposes of this invention and claims thereto, a substituted hydrocarbyl is a radical made of carbon and hydrogen where at least one hydrogen is replaced by a heteroatom. For purposes of this invention and claims thereto a substituted alkyl or aryl group is an alkyl or aryl radical made of carbon and hydrogen where at least one hydrogen is replaced by a heteroatom or a linear, branched, or cyclic substituted or unsubstituted hydrocarbyl group having 1 to 30 carbon atoms.

Carbene Complexes of Lithium and/or Magnesium Salts

The present invention relates to a carbene complex of a lithium or magnesium salt, represented by the formula: [T–M (R)$_c$]$_n$, where R is a monoanionic group; M is Li or Mg, preferably Li; T is a cyclic carbene ligand; c is 1 or 2; and, n is selected from the group of integers comprising 1 to 24, e.g. 1, 2, 3, 4, 5, 6, 7, 8, 9, 10, 11, 12 13, 14, 15, 16, 17, 18, 19, 20, 21, 22, 23, and 24, indicating that the complex of a lithium or magnesium salt of a carbene is dimerized (n=2), trimerized (n=3), tetramerized (n=4), etc.

In particular embodiments, R is at least one of an alkyl sulfonate, aryl sulfonate, alkyl sulfate, aryl sulfate, carboxylate, aryl carboxylate, amidate, amidinate, thiocarboxylate, dithiocarboxylate, borate, chloride, bromide, iodide, nitrate, triflate, or perchlorate. In preferred embodiments, R is a triflate (OTf or TfO). Preferred triflates are represented by the Formula (A) below. Preferred alkyl sulfonates are represented by the Formula (B) below, where R$^2$ is a C$_1$ to C$_{30}$ hydrocarbyl group, fluoro-substituted carbyl group, chloro-substituted carbyl group, aryl group, or substituted aryl group, preferably a C$_1$ to C$_{12}$ alkyl or aryl group, preferably trifluoromethyl, methyl, phenyl, para-methyl-phenyl.

Formula (A)

$$O=\overset{CF_3}{\underset{O}{S}}-O^-$$

Formula (B)

$$O=\overset{R^2}{\underset{O}{S}}-O^-$$

For purposes of this invention and claims thereto, a "cyclic carbene" is defined as a cyclic compound with a neutral dicoordinate carbene center featuring a lone pair of electrons. Preferred cyclic carbenes are represented by the Formula (I) below:

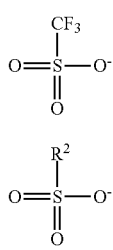

(Formula I)

(for clarity, in the above Formula I a pair of electrons is depicted just below the "C") where e is 0, 1 or 2, d is 1, 2, 3 or 4, Q is C, Si, N, P, O, or S, with available valences (R*) optionally occupied by hydrogen, oxo, hydrocarbyl or substituted hydrocarbyl groups (preferably, each R* is, independently, H or a C$_1$ to C$_{20}$ alkyl); and each E is, independently, selected from the group comprising C, N, S, O, and P, with available valences, if any, optionally occupied by L$^w$, L$^x$, L$^y$, and L$^z$. L$^w$, L$^x$, L$^y$, and L$^z$ are, independently, hydrogen, hydrocarbyl groups or substituted hydrocarbyl groups. In particular embodiments, L$_w$, L$^x$, L$^y$, and L$^z$ are independently selected from the group consisting of hydrocarbyl groups and substituted hydrocarbyl groups having 1 to 40 carbon atoms. In preferred embodiments, L$^w$, L$^x$, L$^y$, and L$^z$ are independently C$_{1-10}$ alkyl, substituted C$_{1-10}$ alkyl, C$_{2-10}$ alkenyl, substituted C$_{2-10}$ alkenyl, C$_{2-10}$ alkynyl, substituted C$_{2-10}$ alkynyl, aryl and substituted aryl. In particularly preferred embodiments, L$^w$, L$^x$, L$^y$, and L$^z$ are independently selected from the group comprising methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, toluoyl, chlorophenyl, 2,6-diethylphenyl, 2,6-diisopropylphenyl, 2-isopropylphenyl, 2-ethyl-6-methylphenyl, 3,5-ditertbutylphenyl, 2-tertbutylphenyl, and 2,3,4,5,6-pentamethylphenyl. Useful substituents include C$_{1-10}$ alkyl, C$_{2-10}$ alkenyl, C$_{2-10}$ alkynyl, aryl, C$_{1-10}$ alkoxy, C$_{2-10}$ alkenyloxy C$_{2-10}$, alkynyloxy, aryloxy, C$_{2-10}$ alkoxycarbonyl, C$_{1-10}$ alkylthio, C$_{1-10}$ alkylsulfonyl, fluoro, chloro, bromo, iodo, oxo, amino, imine, nitrogen heterocycle, hydroxy, thiol, thiono, phosphorous, and carbene groups.

In a preferred embodiment, Q is carbon, each R* is hydrogen, e is 1 or 2 and d is 2.

Examples of cyclic carbenes useful in embodiments of the present invention include:

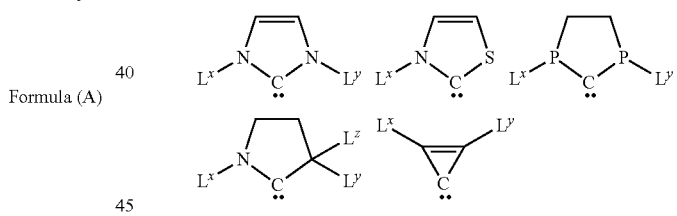

(for clarity, in the above formulae a pair of electrons is depicted just below the "C") where L$^z$, L$^x$ and L$^y$ are as described above. In some embodiments, at least two of L$^x$, L$^y$, and L$^z$ may be joined to form a 3- to 12-membered spirocyclic ring, with available valences optionally occupied by H, oxo, halogens, hydrocarbyl or substituted hydrocarbyl groups. Useful substituents include C$_{1-10}$ alkyl, C$_{2-10}$ alkenyl, C$_{2-10}$ alkynyl, aryl, C$_{1-10}$ alkoxy, C$_{2-10}$ alkenyloxy C$_{2-10}$, alkynyloxy, aryloxy, C$_{2-10}$ alkoxycarbonyl, C$_{1-10}$ alkylthio, C$_{1-10}$ alkylsulfonyl, fluoro, chloro, bromo, iodo, oxo, amino, imine, nitrogen heterocycle, hydroxy, thiol, thiono, phosphorous, and carbene groups.

Preferred cyclic carbenes include N-heterocyclic carbenes (NHCs). For purposes of this invention and claims thereto, "NHCs" are cyclic carbenes of the types described above (such as by Formula I) where each E is N and the available valences on the N are occupied by L$^x$ and L$^y$. Useful NHCs are represented by the formula:

Formula II

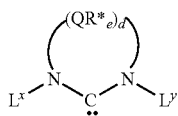

(for clarity, in the above Formula II a pair of electrons is depicted just below the "C") where Q, R*, e, d, $L^x$ and $L^y$ are as described above. In particular embodiments, $L^x$ and $L^y$ are independently selected from the group comprising a hydrocarbyl group and substituted hydrocarbyl group having 1 to 40 carbon atoms. In preferred embodiments, $L^x$ and $L^y$ are independently selected from the group comprising $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, aryl and substituted aryl. In particularly preferred embodiments, $L^x$ and $L^y$ are independently selected from the group comprising methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, toluoyl, chlorophenyl, 2,6-diethylphenyl, 2,6-diisopropylphenyl, 2-isopropylphenyl, 2-ethyl-6-methylphenyl, 3,5-ditertbutylphenyl, 2-tertbutylphenyl, and 2,3,4,5,6-pentamethylphenyl. Useful substituents include $C_{1-10}$ alkyl, $C_{2-10}$ alkenyl, $C_{2-10}$ alkynyl, aryl, $C_{1-10}$ alkoxy, $C_{2-10}$ alkenyloxy $C_{2-10}$, alkynyloxy, aryloxy, $C_{2-10}$ alkoxycarbonyl, $C_{1-10}$ alkylthio, $C_{1-10}$ alkylsulfonyl, fluoro, chloro, bromo, iodo, oxo, amino, imine, nitrogen heterocycle, hydroxy, thiol, thiono, phosphorous, and carbene groups.

Some particularly useful NHCs include:

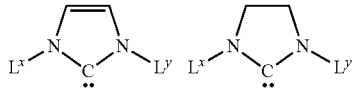

(for clarity, in the above formulae a pair of electrons is depicted just below the "C") where $L^x$ and $L^y$ are as described above.

Other useful NHCs include the compounds described in Hermann, W. A. *Chem. Eur. J.* 1996, 2, 772 and 1627; Enders, D. et al., *Angew. Chem. Int. Ed.* 1995, 34, 1021; Alder R. W., *Angew. Chem. Int. Ed.* 1996, 35, 1121; and Bertrand, G. et al., *Chem. Rev.* 2000, 100, 39.

Particularly preferred cyclic carbenes include cyclic alkyl amino carbenes (CAACs). For purposes of this invention and claims thereto, CAACs are cyclic carbenes as described in Formula I where one E is N and the other is C, and the available valences on the N occupied by $L^x$, and available valences on the C are occupied by $L^y$ and $L^z$. Preferred CAACs are represented by the formula:

Formula III

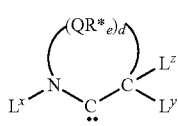

(for clarity, in the above Formula III a pair of electrons is depicted just below the "C" between the N atom and the carbon bound to $L^z$ and $L^y$)

where Q, R*, e, d, $L^x$, $L^z$, and $L^y$ are as described above. In particular embodiments, $L^x$, $L^z$, and $L^y$ are independently selected from the group comprising a hydrocarbyl group and substituted hydrocarbyl group having 1 to 40 carbon atoms. In preferred embodiments, $L^x$, $L^z$, and $L^y$ are independently selected from the group comprising $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, aryl and substituted aryl. In particularly preferred embodiments, $L^x$, $L^z$, and $L^y$ are independently selected from the group comprising methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, toluoyl, chlorophenyl, 2,6-diethylphenyl, 2,6-diisopropylphenyl, 2-isopropylphenyl, 2-ethyl-6-methylphenyl, 3,5-ditertbutylphenyl, 2-tertbutylphenyl, and 2,3,4,5,6-pentamethylphenyl. Useful substituents include $C_{1-10}$ alkyl, $C_{2-10}$ alkenyl, $C_{2-10}$ alkynyl, aryl, $C_{1-10}$ alkoxy, $C_{2-10}$ alkenyloxy $C_{2-10}$, alkynyloxy, aryloxy, $C_{2-10}$ alkoxycarbonyl, $C_{1-10}$ alkylthio, $C_{1-10}$ alkylsulfonyl, fluoro, chloro, bromo, iodo, oxo, amino, imine, nitrogen heterocycle, hydroxy, thiol, thiono, phosphorous, and carbene groups.

Some particularly useful CAACs include:

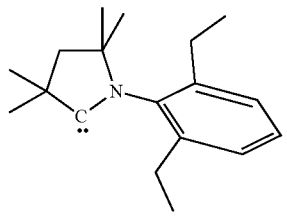

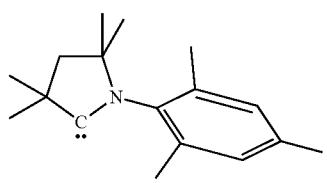

(for clarity, in the above formulae a pair of electrons is depicted just below the "C").

Other useful CAACs include the compounds described in U.S. Pat. No. 7,312,331 and Bertrand et al, *Angew. Chem. Int. Ed.* 2005, 44, 7236-7239.

Other carbenes useful in embodiments of the present invention include thiazolyldenes, P-heterocyclic carbenes (PHCs), and cyclopropenylidenes.

In a particularly preferred embodiment, the carbene complex of a lithium and or magnesium salt is represented by the formula:

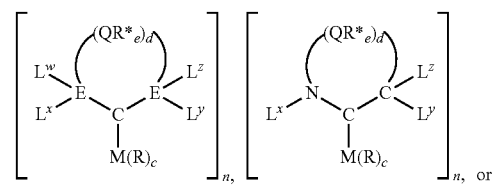

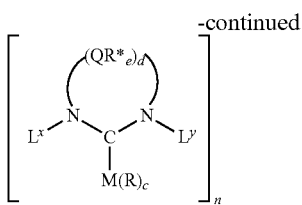

where M is Li or Mg (preferably Li), E, R, c, n, Q, R*, e, d, $L^w$, $L^x$, $L^z$, and $L^y$ are as described above.

The inventors have surprisingly found that certain carbene complexes comprising a lithium and/or magnesium salt form an oligomeric cluster. In preferred embodiments, the carbene complex comprising a lithium salt forms an oligomeric cluster. In particular embodiments, where n is 4, the complex comprising a lithium and/or magnesium salt of a carbene forms a cube-like oligomeric cluster, where M and R groups occupy the proximate vertices of the cube, as represented by:

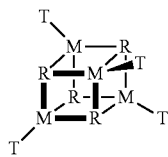

where M, R and T are as described above.

In particularly preferred embodiments, where M is Li, n is 4, and R is OTf, the complex of the present invention forms a cube-like oligomeric cluster, where Li and OTf groups occupy the proximate vertices of the cube, as represented by:

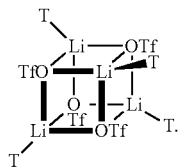

In even more particularly preferred embodiments, T is a CAAC of the type:

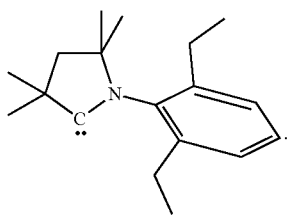

Preparation of Carbene Complexes of a Lithium and/or Magnesium Salt

The carbene complexes of lithium and/or magnesium salts described above are typically prepared by contacting a protonated cyclic carbene salt with a lithium or magnesium base (preferably at −40 to 40° C., preferably above 0° C.) in a non-polar solvent. For purposes of this invention and the claims thereto a non-polar solvent is defined as a solvent that contains only carbon, hydrogen and optional halogen atoms (such as an alkane, arene or halogenated hydrocarbons or halogenated aromatics), while a polar solvent is defined a solvent that contains at least one Group 15 or 16 heteroatom (such as oxygen, or sulfur). Both aliphatic and aromatic non-polar solvents are suitable for use herein. Preferred non-polar solvents include benzene, toluene, hexane, pentane, isopentane, and octane.

The isolation of the carbene complexes of lithium and/or magnesium salts is typically accomplished by crystallization or precipitation of the complex from a non-polar solvent or mixture of non-polar solvents.

In a preferred embodiment, the carbene complexes of lithium and/or magnesium salts described above are prepared by the stepwise addition of a protonated cyclic carbene salt, as either a solid, a solution, or a slurry, to a solution of a lithium or magnesium base in a non-polar solvent.

In a preferred embodiment, the carbene complexes of lithium and/or magnesium salts described above are prepared under conditions such that the temperature is between −40 to 40° C. (preferably from 0 to 40° C.), the pressure is ambient, and the concentration of each reactant is between 0.00001 M and 1.0 M.

Suitable lithium and magnesium bases include, but are not limited to, lithium amides, magnesium amides, alkyllithiums, aryl lithiums, dialkylmagnesiums, diarylmagnesiums, and magnesium(alkyl)amides.

The inventors have surprisingly discovered that the carbene complexes of lithium and/or magnesium salts of the present invention display unexpected and unusual stability in both coordinating and non-coordinating solvents at or above ambient temperatures. Specifically, the inventors have surprisingly discovered that complexes of lithium salts of CAACs with N-substitution such as 2,6-diethylphenyl, are remarkably stable in solution at ambient temperatures. For example, in solution stability studies of a complex of a particular embodiment of the present invention (Compound 1, reported in Examples 2 & 3, below) only 14% decomposition was observed in benzene at ambient temperature over a period of 4 days. In another embodiment, less than 5% decomposition was observed in tetrahydrofuran at ambient temperature over a period of 72 hours. Without wishing to be bound by theory, the inventors believe that the ordered oligomeric clustering observed in the carbene complexes of lithium and/or magnesium salts may provide added stability to the complex as compared to the free carbene.

Hence in a preferred embodiment, the carbene complexes of a lithium and/or magnesium salt described above are stable at 23° C. or more. In a preferred embodiment, the carbene complexes of a lithium and/or magnesium salt described above are stable at 30° C. or more, preferably at 50° C. or more. In a preferred embodiment, the carbene complexes of a lithium and/or magnesium salt described above are stable at 23° C., preferably at 30° C., preferably at 50° C. In a preferred embodiment, the carbene complexes of a lithium and/or magnesium salt described above are stable at from −40 to 80° C., preferably from 0 to 60° C., preferably from 20 to 50° C. (Stable is defined to be 50% or less decomposition when stored in 0.01 benzene at the selected temperature for a period of 1 hour. When a temperature range (e.g., −40 to 80° C.) is indicated, stability is determined by measuring % decomposition at each end of the range. Both values must be at or below the value in question, e.g. 50% or less). In a preferred embodiment, the carbene complexes of a lithium and/or magnesium salt described above have 50% or less (preferably 40% or less, preferably 30% or less, preferably 20% or less, preferably 10% or less, preferably 5% or less) decomposition when stored in 0.01 benzene (alternately tetrahydrofuran, alternately hexane) at the selected temperature for a period of 24 hours.

Transition-Metal-Carbene Complexes

The carbene complexes of lithium and/or magnesium salts described above may be used to prepare transition-metal-carbene complexes. In a particular embodiment, a method for the preparation of a transition-metal-carbene complex comprises combining a transition metal reactant and at least one carbene complex of a lithium and/or magnesium salt as described above, wherein the carbene is transferred from the lithium and/or magnesium salt to the transition metal reactant.

For purposes of this invention and claims thereto, a "transition metal reactant" is a compound comprising at least one transition metal with one or more coordinated ligands (the coordinated ligands are typically neutral or anionic non-metal species). For purposes of this invention and claims thereto, a "transition metal" is an element from Groups 3, 4, 5, 6, 7, 8, 9, 10, 11, or 12 (including the lanthanides and actinides) of the Periodic Table, as referenced by the IUPAC in *Nomenclature of Inorganic Chemistry: Recommendations* 1990, G. J. Leigh, Editor, Blackwell Scientific Publications, 1990. Transition metal reactants useful in embodiments of the present invention comprise transition metals (M* in the formulae below) from Group 3-12 (preferably M* is Sc, Y, Ti, Zr, Hf, V, Nb, Ta, Cr, Mo, W, Mn, Re, Co, Rh, Ir, Ni, Pd, Pt, Cu, Ag, Au, Fe, Ru and/or Os), more particularly Groups 6-11 (preferably M* is Cr, Co, Ni, Cu, Mn, Rh, Pd, Pt, Ag, Au, Fe, Ru and/or Os), even more particularly Group 8 (preferably M* is Fe, Ru and/or Os, preferably M* is Ru).

The coordinated ligands are typically neutral or anionic non-metal species, such as trialkylphosphines, pyridines, halides, alkyls, aryls, alkylidenes, ethers, and thio ethers. Preferred examples include tricyclohexylphosphine, chlorides, substituted benzylidenes, ether substituted benzylidenes. The coordinated ligands feature at least one pair of lone electrons that can form a dative or covalent bond with the transition metal. Preferably, the transition metal reactant features at least one labile neutral ligand, such as tricyclohexyl phosphine, which is exchanged for the cyclic carbene in the reaction.

In a preferred embodiment, the transition metal reactant is represented by the formula:

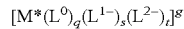

where M* is a transition metal as defined above; $L^0$ is a neutral ligand; $L^{1-}$ is a monoanionic ligand; $L^{2-}$ is a dianionic ligand; g is the overall charge of the molecule (preferably 0, 1, or 2); q is 0, 1, 2, 3, or 4; s is 0, 1, 2, 3, or 4; and t is 0, 1, 2, 3, or 4; where g+s+2(t) is equal to the valence of the transition metal, M*. For purposes of this invention and the claims thereto, "valence" is equivalent to oxidation number. The overall coordination number of the transition metal is preferably 4, 5, 6, or 7. Preferably, the valence of the metal will be 0, 1, 2, 3, or 4. Preferably, each ligand may be monodentate, bidentate, tridentate, tetradentate, pentadentate, or hexadentate.

In a preferred embodiment, the transition metal reactant is a ruthenium phosphine complex. Preferred ruthenium phosphine complexes are typically the combination of ruthenium and a phosphine. For purposes of this invention and claims thereto, "phosphines" are represented by the formula $PR^9{}_3$, wherein each $R^9$ is independently hydrogen, a $C_1$ to $C_{12}$ hydrocarbyl group, a substituted $C_1$ to $C_{12}$ hydrocarbyl group, or a halide. Preferred ruthenium phosphine complexes are represented by the formula:

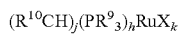

where X is a halogen (preferably chlorine or bromine); $R^9$ is as defined above; h is 1, 2, or 3 (preferably 1 or 2); j is 0, 1, or 2; k=1 or 2; and $R^{10}CH$ is a dianionic group, such as an alkylidene, substituted alkylidene, or a chelating substituted alkylidene ligand.

Examples of ruthenium phosphine complexes useful in embodiments herein include bis(tricyclohexylphosphine) benzylidine ruthenium dichloride, dichloro(o-isopropoxyphenylmethylene)(tricyclohexylphosphine) ruthenium dichloride, tris(triphenylphosphine) ruthenium dichloride, {[2-(1-propoxy)-5-(N,N-dimethylaminosulfonyl)phenyl] methylene}(tricyclohexylphosphine) ruthenium dichloride, bis(i-butylphoban)(3-phenyl-1H-inden-1-ylidene)ruthenium dichloride, and bis(tricyclohexylphosphine)(3-phenyl-1H-inden-1-ylidene)ruthenium dichloride.

In some embodiments, the transition metal reactant may be supported on an inert material. The inert material tends to render the transition metal reactant heterogeneous, which often simplifies product recovery. Suitable support materials include, without limitation, silicas, aluminas, silica-aluminas, aluminosilicates, including zeolites and other crystalline porous aluminosilicates; as well as titanias, zirconia, magnesium oxide, carbon, and cross-linked, reticular polymeric resins, such as functionalized cross-linked polystyrenes, e.g., chloromethyl-functionalized cross-linked polystyrenes. The transition metal reactant may be deposited onto the support by any method known to those of ordinary skill in the art, including, for example, impregnation, ion-exchange, deposition-precipitation, and vapor deposition. Alternatively, the transition metal reactant may be chemically bound to the support via one or more covalent chemical bonds, for example, the compound may be immobilized by one or more covalent bonds with one or more of the ligands bound to the transition metal.

The transition metal reactant and the carbene complexes of lithium and/or magnesium salts described above may be used in various synthetic processes. For example, a transition metal reactant (as described above) and a carbene complex of a lithium and/or magnesium salt of a carbene (as described above), are combined to form a transition-metal-carbene complex wherein the carbene is transferred from the salt to the transition metal reactant. In some embodiments, the carbene is transferred from the lithium or magnesium salt to the transition metal reactant in situ. The transition-metal-carbene complex is typically used in other processes such as metathesis reactions, for example, the metathesis of olefins.

The transition metal reactant and the carbene complex of a lithium and/or magnesium salt may be combined in any manner known in the art. In some embodiments, the transition metal reactant and the lithium or magnesium salt of a carbene may be combined in a non-coordinating solvent, in a coordinating solvent, or a mixture thereof. The solvent may be polar or non-polar or may be a blend of polar and non-polar solvents. Hydrocarbon solvents, both aliphatic and aromatic are suitable non-polar solvents. Alkanes, such as hexane, pentane, isopentane, and octane, are useful. Alternately, mixtures of polar and non-polar solvents can be used. Particularly, a mixture of a non-polar aliphatic or aromatic solvent with a polar solvent particularly diethyl ether, can be used. Useful polar solvents include diethyl ether, methyl t-butyl ether, tetrahydrofuran, di-n-butyl ether, methyl propyl ether, di-n- propyl ether, diisopropyl ether, ethyl acetate, and acetone. Preferred non-polar solvents include toluene, hexane, pentane, isopentane, and octane.

In some embodiments, the carbene complex comprising a lithium and/or magnesium metal salt of a carbene may be generated in situ. In a preferred embodiment, the carbene complexes of lithium and/or magnesium salts described above are typically formed in situ by contacting a protonated cyclic carbene salt with a lithium or magnesium base (preferably at −40 to 40° C.) in a non-polar solvent. The solution containing the in-situ formed lithium or magnesium salt complex can then be used in applications analogous to the isolated lithium or magnesium salt complex. Preferably, the in-situ reaction occurs at a temperature of −40 to 40° C., preferably 0 to 40° C., preferably 20 to 30° C. By in-situ is meant that the product formed in a reaction is used without being isolated from the reaction solution. Preferably, the product formed in the reaction is used without being substantially separated from the reaction medium (such as a solvent); preferably, the product formed in the reaction is used without being separated from the majority of the reaction medium.

In some embodiments, the transfer of the carbene to the transition metal reactant may occur by coordination to the transition metal. In other embodiments, the transfer of the carbene to the transition metal reactant may occur by a substitution reaction, such as ligand exchange.

Preferably, the reaction to form a transition-metal-carbene complex by combination of a carbene complex of a lithium or magnesium salt with a transition-metal reactant occurs at a temperature of −40 to 120° C., preferably 0 to 80° C., preferably 20 to 60° C.

In embodiments, the reaction to form a transition-metal-carbene complex by combination of a carbene complex of a lithium and/or magnesium salt with a transition-metal reactant occurs at a pressure of 0.01 to 100 atmospheres (1.01 to 10132.5 kPa), preferably 0.8 to 2 atmospheres (81.1 to 202.7 kPa), preferably at ambient pressure.

Preferably, the reaction to form a transition-metal-carbene complex by combination of a carbene complex of a lithium or magnesium salt with a transition-metal reactant occurs at a concentration of reactants of 0.0000001 to 10 molar, preferably 0.0001 to 1 molar, preferably 0.01 to 1 molar.

Preferred transition-metal-carbene complexes produced herein are represented by the formula:

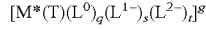

$[M^*(T)(L^0)_q(L^{1-})_s(L^{2-})_t]^g$ where $M^*$ is a transition metal as defined above; T is a cyclic carbene ligand as defined above; $L^0$ is a neutral ligand; $L^{1-}$ is a monoanionic ligand; $L^{2-}$ is a dianionic ligand; q is 0, 1, 2, 3, or 4; s is 0, 1, 2, 3, or 4; t is 0, 1, 2, 3, or 4; and g is the overall charge of the molecule (preferably 0, 1, or 2). Preferably, each ligand may be monodentate, bidentate, tridentate, tetradentate, pentadentate, or hexadentate. The overall coordination number of the transition metal is preferably 4, 5, 6, or 7. The valence of the metal M is g+s+2(t). Preferably, the valence of the metal will be 0, 1, 2, 3, or 4.

Preferred transition-metal-carbene complexes produced herein include: 2-(2,6-diethylphenyl)-3,3,5,5-tetramethylpyrrolidine[2-(i-propoxy)-5-(N,N-dimethylaminosulfonyl)phenyl]methylene ruthenium dichloride (compound D), 2-(2,6-diethylphenyl)-3,3,5,5-tetramethylpyrrolidine(o-isopropoxyphenylmethylene)ruthenium dichloride, 2-(2,4,6-trimethylphenyl)-3,3,5,5-tetramethylpyrrolidine[2-(i-propoxy)-5-(N,N-dimethylaminosulfonyl)phenyl]methylene ruthenium dichloride, 2-(2,4,6-trimethylphenyl)-3,3,5,5-tetramethylpyrrolidine(o-isopropoxyphenylmethylene)ruthenium dichloride, 2-(2-isopropylphenyl)-3,3,5,5-tetramethylpyrrolidine[2-(i-propoxy)-5-(N,N-dimethylaminosulfonyl)phenyl]methylene ruthenium dichloride, 2-(2-isopropylphenyl)-3,3,5,5-tetramethylpyrrolidine(o-isopropoxyphenylmethylene)ruthenium dichloride, 2-(2-ethyl-6-methylphenyl)-3,3,5,5-tetramethylpyrrolidine[2-(i-propoxy)-5-(N,N-dimethylaminosulfonyl)phenyl]methylene ruthenium dichloride, 2-(2-ethyl-6-methylphenyl)-3,3,5,5-tetramethylpyrrolidine(o-isopropoxyphenylmethylene)ruthenium dichloride, 2-(2,4-dimethylphenyl)-3,3,5,5-tetramethylpyrrolidine[2-(i-propoxy)-5-(N,N-dimethylaminosulfonyl)phenyl]methylene ruthenium dichloride, and 2-(2,4-dimethylphenyl)-3,3,5,5-tetramethylpyrrolidine(o-isopropoxyphenylmethylene)ruthenium dichloride.

The transition metal carbene complexes produced herein may be used as catalysts in many other reactions such as those described by Nolan and coworkers in *Chemical Reviews* 2009, 109, 3612-3676. These include polymerizations, cyclizations, C—C bond formations, hydrogenations, isomerizations, hydrosilylations, hydroformylations, arylations of carbonyl compounds with boron reagents, reductions, oxidations, hydrogen/deuterium exchanges, cross coupling reactions, allylic alkylations, carbonylations, C—H bond activations, cycloisomerizations, addition reactions, telomerizations, conjugate additions, cycloadditions, and allylic alkylations.

The transition-metal-carbene complexes produced herein may be used in many other reactions, including the metathesis of olefins. In particular these transition metal carbene complexes can be combined with a seed oil, triacylglyceride, fatty acid, fatty acid ester, and/or fatty acid alkyl ester, and an alkene such as ethylene, to make linear alpha-olefins (having at least 1 more carbon atom than the starting alkene), preferably 1-decene, 1-butene, and 1-heptene. Such linear alpha olefins can then be used to make polyalphaolefins.

In other embodiments, this invention relates to:
1. A process to produce alpha-olefin (preferably linear alpha olefin) comprising contacting a seed oil with the transition-metal-carbene complexes produced herein (e.g., using a carbene complex of a lithium and or magnesium salt as a synthon), preferably with one or more of 2-(2,6-diethylphenyl)-3,3,5,5-tetramethylpyrrolidine [2-(i-propoxy)-5-(N,N-dimethylaminosulfonyl)phenyl]methylene ruthenium dichloride (compound D), 2-(2,6-diethylphenyl)-3,3,5,5-tetramethylpyrrolidine(o-isopropoxyphenylmethylene)ruthenium dichloride, 2-(2,4,6-trimethylphenyl)-3,3,5,5-tetramethylpyrrolidine[2-(i-propoxy)-5-(N,N-dimethylaminosulfonyl)phenyl]methylene ruthenium dichloride, 2-(2,4,6-trimethylphenyl)-3,3,5,5-tetramethylpyrrolidine(o-isopropoxyphenylmethylene)ruthenium dichloride, 2-(2-isopropylphenyl)-3,3,5,5-tetramethylpyrrolidine[2-(i-propoxy)-5-(N,N-dimethylaminosulfonyl)phenyl]methylene ruthenium dichloride, 2-(2-isopropylphenyl)-3,3,5,5-tetramethylpyrrolidine(o-isopropoxyphenylmethylene)ruthenium dichloride, 2-(2-ethyl-6-methylphenyl)-3,3,5,5-tetramethylpyrrolidine[2-(i-propoxy)-5-(N,N-dimethylaminosulfonyl)phenyl]methylene ruthenium dichloride, 2-(2-ethyl-6-methylphenyl)-3,3,5,5-tetramethylpyrrolidine(o-isopropoxyphenylmethylene)ruthenium dichloride, 2-(2,4-dimethylphenyl)-3,3,5,5-tetramethylpyrrolidine[2-(i-propoxy)-5-(N,N-dimethylaminosulfonyl)phenyl]methylene ruthenium dichloride, and 2-(2,4-dimethylphenyl)-3,3,5,5-tetramethylpyrrolidine(o-isopropoxyphenylmethylene)ruthenium dichloride.

2. The process of paragraph 1, wherein the seed oil is selected from the group consisting of canola oil, corn oil, soybean oil, rapeseed oil, algae oil, peanut oil, mustard oil, sunflower oil, tung oil, perilla oil, grapeseed oil, linseed oil, safflower oil, pumpkin oil, palm oil, Jathropa oil, high-oleic soybean oil, high-oleic safflower oil, high-oleic sunflower oil, mixtures of animal and vegetable fats and oils, castor bean oil, dehydrated castor bean oil, cucumber oil, poppyseed oil, flaxseed oil, lesquerella oil, walnut oil, cottonseed oil, meadowfoam, tuna oil, sesame oils and mixtures thereof.

3. The process of paragraph 1, wherein the seed oil is selected from the group consisting of palm oil and algae oil.

4. A process to produce alpha-olefin comprising contacting a triacylglyceride with an alkene and the transition-metal-carbene complexes produced herein (such as the complexes described in paragraph 1), preferably wherein the alpha olefin produced has at least one more carbon atom than the alkene.

5. The process of paragraph 4, wherein the triacylglyceride is contacted with alcohol and converted to an fatty acid ester or fatty acid alkyl ester prior to contacting with the transition-metal-carbene complex.

6. The process of paragraph 4, wherein the triacylglyceride is contacted with water or an alkaline reagent and converted to a fatty acid prior to contacting with the transition-metal-carbene complex.

7. A process to produce alpha-olefin comprising contacting an unsaturated fatty acid with an alkene and a transition-metal-carbene complex (preferably one or more of the compounds described in paragraph 1), preferably wherein the alpha olefin produced has at least one more carbon atom than the alkene.

8. A process to produce alpha-olefin comprising contacting a triacylglyceride with a transition-metal-carbene complex (preferably one or more of the compounds described in paragraph 1), preferably wherein the alpha olefin produced has at least one more carbon atom than the alkene.

9. A process to produce alpha-olefin comprising contacting an unsaturated fatty acid ester and or unsaturated fatty acid alkyl ester with an alkene and a transition-metal-carbene complex (preferably one or more of the compounds described in paragraph 1), preferably wherein the alpha olefin produced has at least one more carbon atom than the alkene.

10. The process of any of paragraphs 1 to 9, wherein the alpha olefin is a linear alpha-olefin having 4 to 24 carbon atoms.

11. The process of any of paragraphs 1 to 10, wherein the alkene is ethylene, propylene, butene, hexene, or octene.

12. The process of any of paragraphs 1 to 11, wherein the fatty acid ester is a fatty acid methyl ester.

13. The process of any of paragraphs 1 to 12, wherein the triacylglyceride, fatty acid, fatty acid alkyl ester, fatty acid ester is derived from biodiesel.

14. The process of any of paragraphs 1 to 13, wherein the alpha-olefin is butene-1, decene-1, and or heptene-1.

15. A process to produce $C_4$ to $C_{24}$ linear alpha-olefin comprising contacting a feed material with an alkene selected from the group consisting of ethylene, propylene butene, pentene, hexene, heptene, octene, nonene and mixtures thereof and a transition-metal-carbene complex (preferably one or more of the compounds described in paragraph 1), wherein the feed material is a triacylglyceride, fatty acid, fatty acid alkyl ester, and/or fatty acid ester derived from seed oil or algae.

Without wishing to be bound by theory, the inventors believe that the ordered oligomeric clustering observed in the carbene complex comprising a lithium and/or magnesium salt may provide added stability to the complex as compared to the free carbene.

Decomposition of non-inventive carbene reactants usually occurs through a dimerization of the free carbenes. However, without wishing to be bound by theory, the inventors believe that the oligomeric clusters of preferred embodiments herein stabilize the carbene by preventing the dimerization and/or other decomposition reactions. Instead, the carbene complexes of the lithium and/or magnesium salts are stabilized in this oligomeric cluster within a timeframe sufficient for synthetic reactions, in particular substitution reactions such as ligand exchange, to take place. Accordingly, the complexes of the present invention provide carbene sources which are stable at ambient and super-ambient temperatures. Therefore the complexes of the present invention fulfill a key need for carbene sources that are stable at the ambient or super-ambient temperatures at which synthetic reactions such as ligand exchange substitution reactions can proceed at a reasonable rate.

Indeed, the inventors report the synthesis of Compound D, Comparative Example 1 below, according to conventional synthetic routes, with a yield of 6.4%. On preparing Compound D using the novel method of preparation described herein, Example 2 below, the inventors report a dramatically increased yield of 89%. Furthermore, on preparing Compound D using a carbene complex of a lithium and/or magnesium salt generated in situ (Example 3, below), the inventors report an extraordinary 79% yield. The inventors believe that the high yielding ligand exchange reactions described herein may be at least partially attributable to these the increased stability of the carbene complex of a lithium and/or magnesium salt as compared to the free carbene.

In a preferred embodiment, the yield ((moles of transition-metal-carbene complex divided by moles of transition metal reactant) times 100) is at least 20%, preferably at least 30%, preferably at least 40%, preferably at least 50%, preferably at least 60%, preferably at least 70%, preferably at least 80%.

In another embodiment this invention relates to:

1. A carbene complex of metal salt represented by the formula:

wherein, R is a monoanionic group; c is 1 or 2; M is a Li or Mg; T is a cyclic carbene ligand; and n is selected from the group of integers comprising 1 to 24 wherein the complex has 50% or less decomposition when stored in 0.01 molar benzene at 23° C. for a period of 1 hour.

2. The complex of paragraph 1, wherein T is represented by Formula (I):

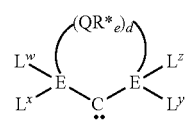

(Formula I)

where e is 0, 1, or 2; d is 1, 2, 3, or 4; Q is C, Si, N, P, O, or S; each R* is a hydrogen, oxo, hydrocarbyl or substituted hydrocarbyl group; and each E is, independently, C, N, S, O, or P, with available valences, if any, occupied by $L^w$, $L^x$, $L^y$, and $L^z$, where $L^w$, $L^x$, $L^y$, and $L^z$ are, independently, hydrogen, hydrocarbyl groups or substituted hydrocarbyl groups.

3. The complex of paragraph 1 or 2, wherein $L^w$, $L^x$, $L^y$, and $L^z$ are independently selected from the group consisting of hydrocarbyl groups and substituted hydrocarbyl groups having 1 to 40 carbon atoms.

4. The complex of any of paragraphs 1 to 3, wherein $L^w$, $L^x$, $L^y$, and $L^z$ are independently $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, aryl and substituted aryl.

5. The complex of any of paragraphs 1 to 4, wherein $L^w$, $L^x$, $L^y$, and $L^z$ are independently selected from the group comprising methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, toluoyl, chlorophenyl, 2,6-diethylphenyl, 2,6-diisopropylphenyl, 2-isopropylphenyl, 2-ethyl-6-methylphenyl, 3,5-ditertbutylphenyl, 2-tertbutylphenyl, and 2,3,4,5,6-pentamethylphenyl. Useful substituents include $C_{1-10}$ alkyl, $C_{2-10}$ alkenyl, $C_{2-10}$ alkynyl, aryl, $C_{1-10}$ alkoxy, $C_{2-10}$ alkenyloxy $C_{2-10}$, alkynyloxy, aryloxy, $C_{2-10}$ alkoxycarbonyl, $C_{1-10}$ alkylthio, $C_{1-10}$ alkylsulfonyl, fluoro, chloro, bromo, iodo, oxo, amino, imine, nitrogen heterocycle, hydroxy, thiol, thiono, phosphorous, and carbene groups.

6. The complex of any of paragraphs 1 to 5, wherein the complex has 40% or less decomposition when stored in 0.01 molar benzene at 30° C. for a period of 1 hour.

7. The complex of any of paragraphs 1 to 6, wherein the complex has 10% or less decomposition when stored in 0.01 molar benzene at 30° C. for a period of 1 hour.

8. The complex of any of paragraphs 1 to 7, wherein each R is at least one of an alkyl sulfonate, aryl sulfonate, alkyl sulfate, aryl sulfate, carboxylate, aryl carboxylate, amidate, amidinate, thiocarboxylate, dithiocarboxylate, borate, chloride, bromide, iodide, nitrate, triflate, and perchlorate.

9. The complex of any of paragraphs 1 to 8, wherein M is lithium.

10. The complex of any of paragraphs 1 to 9, wherein the salt forms an oligomeric cluster.

11. The complex of any of paragraphs 1 to 10, wherein n is 4 and the salt forms a cube-like oligomeric cluster in which M and R groups occupy the proximate vertices of the cube, as represented by:

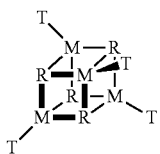

where M, R and T are as defined in paragraph 1.

12. The complex of paragraph 11, wherein each M is Li, and each T is:

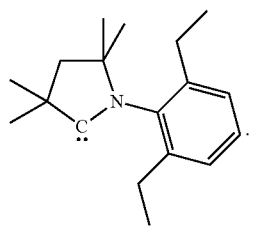

13. The complex of any of paragraphs 1 to 12, wherein the salt forms a cube-like oligomeric cluster in which T is as defined in claim 1, each M is Li and each R is triflate, and the M and R groups occupy the proximate vertices of the cube, as represented by:

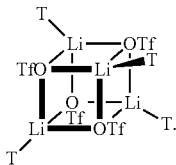

14. The complex of any of paragraphs 1 to 13, wherein the complex is represented by the formula:

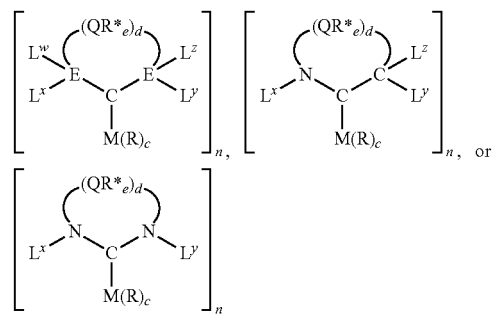

where n is 1, 2, 3, 4, 5, 6, 7, 8, 9, 10, 11, 12, 13, 14, 15, 16, 17, 18, 19, 20, 21, 22, 23, or 24; e is 0, 1, or 2; d is 1, 2, 3, or 4; Q is C, Si, N, P, O, or S; each R* is a hydrogen, oxo, hydrocarbyl or substituted hydrocarbyl group; and each E is, independently, C, N, S, O, or P, with available valences, if any, occupied by $L^w$, $L^x$, $L^y$, and $L^z$, where $L^w$, $L^x$, $L^y$, and $L^z$ are, independently, hydrogen, hydrocarbyl groups or substituted hydrocarbyl groups.

15. A transition-metal-carbene complex prepared from a carbene complex of a lithium and/or magnesium salt, said transition-metal-carbene complex represented by the formula:

$$[M^*(T)(L^0)_q(L^{1-})_s(L^{2-})_t]^g$$

where M* is a transition metal from Group 6, 7, 8, 9, 10, 11, or 12; T is a cyclic carbene ligand; $L^0$ is a neutral ligand; $L^{1-}$ is a monoanionic ligand; $L^{2-}$ is a dianionic ligand; q is 0, 1, 2, 3, or 4; s is 0, 1, 2, 3, or 4; t is 0, 1, 2, 3, or 4; g is the overall charge of the molecule.

16. The transition-metal-carbene complex of paragraph 15, wherein T is represented by Formula (I):

(Formula I)

where e is 0, 1, or 2; d is 1, 2, 3, or 4; Q is C, Si, N, P, O, or S; each R* is a hydrogen, oxo, hydrocarbyl or substituted hydrocarbyl group; and each E is, independently, C, N, S, O, or P, with available valences, if any, occupied by $L^w$, $L^x$, $L^y$, and $L^z$, where $L^w$, $L^x$, $L^y$, and $L^z$ are, independently, hydrogen, hydrocarbyl groups or substituted hydrocarbyl groups.

17. A process to make a transition-metal-carbene complex comprising contacting:
   1) a stable carbene complex of metal salt of any of paragraphs 1 to 14 with
   2) a transition metal reactant represented by the formula:

$[M^*(L^0)_q(L^{1-})_s(L^{2-})_t]^g$ where M* is a transition metal selected from Group 6, 7, 8, 9, 10, 11, or 12; $L^0$ is a neutral ligand; $L^{1-}$ is a monoanionic ligand; $L^{2-}$ is a dianionic ligand; g is the overall charge of the molecule; q is 0, 1, 2, 3, or 4; s is 0, 1, 2, 3, or 4; and t is 0, 1, 2, 3, or 4, where g+s+2(t) is equal to the valence of the transition metal, M*.
18. The process of paragraph 17, wherein the stable carbene complex of metal salt and the transition metal reactant are contacted at 0° C. or more.
19. The process of paragraph 17, wherein the stable carbene complex of metal salt is not isolated from the reaction medium it was made in prior to contacting with the transition metal reactant.
20. The process of paragraph 17, wherein the stable carbene complex of metal salt is not crystallized into a solid prior to contacting with the transition metal reactant.
21. The process of any of paragraphs 17 to 20, wherein the yield is at least 20%, where yield=((moles of transition-metal-carbene complex/moles of transition metal reactant)×100).
22. The process of any of paragraphs 17 to 21, wherein the yield is at least 50%, where yield=((moles of transition-metal-carbene complex/moles of transition metal reactant)×100).
23. The process of any of paragraphs 17 to 22, wherein T is represented by Formula (I):

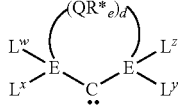

(Formula I)

where e is 0, 1, or 2; d is 1, 2, 3, or 4; Q is C, Si, N, P, O, or S; each R* is a hydrogen, oxo, hydrocarbyl or substituted hydrocarbyl group; and each E is, independently, C, N, S, O, or P, with available valences, if any, occupied by $L^w$, $L^x$, $L^y$, and $L^z$, where $L^w$, $L^x$, $L^y$, and $L^z$ are, independently, hydrogen, hydrocarbyl groups or substituted hydrocarbyl groups.
24. A process to produce alpha-olefin comprising contacting algae and or a seed oil with the transition-metal-carbene complex of paragraph 15 or 16 or the transition-metal-carbene complex produced by any of any of paragraphs 17 to 23.
25. A process to produce $C_4$ to $C_{24}$ linear alpha-olefin comprising contacting a feed material with an alkene selected from the group consisting of ethylene, propylene butene, pentene, hexene, heptene, octene, nonene and mixtures thereof and a transition-metal-carbene complex, wherein the feed material is a triacylglyceride, fatty acid, fatty acid alkyl ester, and/or fatty acid ester derived from seed oil or algae, and wherein the transition-metal-carbene complex is a transition-metal-carbene complex of paragraph 15 or 16 or a transition-metal-carbene complex produced by any of any of paragraphs 17 to 23.

EXPERIMENTAL SECTION

For purposes of this invention and the claims thereto, THF is tetrahydrofuran, iPr or $^iPr$ is isopropyl, Me is methyl, Et is ethyl, $Tf_2O$ is trifluoromethanesulfonic anhydride, TfO is triflate, and Zhan-1C is {[2-(i-propoxy)-5-(N,N-dimethylaminosulfonyl)phenyl]methylene}(tricyclohexylphosphine)ruthenium dichloride.

Typical dry-box procedures for synthesis of air-sensitive compounds were followed including using dried glassware (120° C., >4 hours) and anhydrous solvents purchased from Sigma Aldrich (St. Louis, Mo.) which were further dried over 3 A sieves. All reagents were purchased from Sigma-Aldrich, unless otherwise noted. $^1H$ and $^{13}C$ spectra were recorded on Bruker 250 and 500 spectrometers. Single-crystal X-ray diffraction data was recorded on a Rigaku SCXmini diffractometer.

Synthesis of Precursors

Synthesis of (E)-2,6-diethyl-N-(2-methylpropylidene) aniline (A): Benzene (150 mL) was added to 2,6-diethylaniline (18.59 g, 124.6 mmol) and 3 angstrom molecular sieves (ca. 50 mL). Isobutyraldehyde (9.43 g, 131 mmol) and p-toluenesulfonic acid monohydrate (20 mg, 0.011 mmol) were then added. The flask was sealed and heated to 50° C. After stirring overnight the very pale yellow solution was filtered and the volatiles were removed under reduced pressure to afford 22.5 g of compound A (84.6%) as a clear, pale yellow oil.

$^1H$ NMR ($C_6D_6$): δ 7.21 (1H, d), 7.02 (2H, m), 2.47 (4H, q), 2.39 (1H, m), 1.11 (6H, t), 1.01 (6H, d).

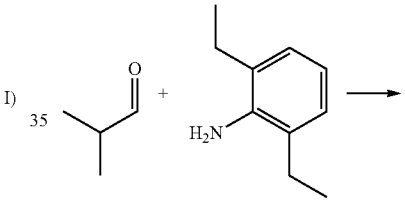

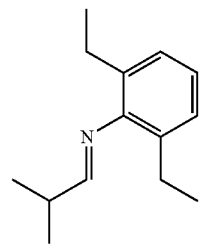

A

Synthesis of lithium (2,6-diethylphenyl)(2-methylprop-1-enyl)amide (B): Benzene (70 mL) and compound A (6.63 g, 32.6 mmol) were combined. Solid lithium diisopropylamide (4.01 g, 37.4 mmol) was then added. The mixture was heated to 50° C. to form a cloudy red-orange solution. After a few hours the solution was filtered through diatomaceous earth to afford a clear yellow solution. The volatiles were evaporated to give a yellow solid. Pentane (15 mL) was added and the mixture was stirred briefly and then cooled to −10° C. overnight. The product was then collected on a glass frit and washed with pentane (2×20 mL) to yield 5.50 g of compound B (80.6%) as a white solid that was dried under reduced pressure and used without further characterization.

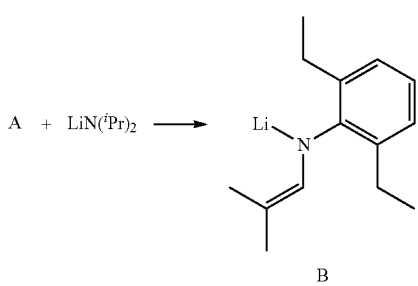

Synthesis of 1-(2,6-diethylphenyl)-2,2,4,4-tetramethyl-3,4-dihydro-2H-pyrrolium triflate (C): Et$_2$O (100 mL) was added to compound B (5.50 g, 26.3 mmol) to form a clear yellow solution. A solution of 1,2-epoxy-2-methylpropane (1.90 g, 26.3 mmol) in Et$_2$O (5 mL) was added dropwise over about 10 seconds, and the mixture was stirred overnight. The mixture was then cooled to −80° C. and trifluoromethanesulfonic anhydride (7.42 g, 26.3 mmol) was added dropwise. The mixture was warmed to ambient temperature over 1 hour. A thick suspension formed. After stirring for an additional hour, a solid was collected on a glass frit and washed with Et$_2$O (3×15 mL). The solid was dried under reduced pressure. The dried solid was then extracted with CH$_2$Cl$_2$ (60 mL) and filtered through diatomaceous earth. The filter cake was washed with CH$_2$Cl$_2$ (2×30 mL). The combined CH$_2$Cl$_2$ extracts were evaporated to an oil and Et$_2$O (15 mL) was added which caused a white crystalline solid to form. The ether solution was cooled to −10° C. overnight. The white solid was then collected and dried under reduced pressure to afford 1.48 g of product C. To obtain additional product the filter cake was loaded into a thimble. This was placed in a Soxhlet extractor and the solid was extracted with hot CH$_2$Cl$_2$ overnight. The resulting CH$_2$Cl$_2$ extract was evaporated and Et$_2$O (10 mL) was added to afford additional product as off-white crystals. The combined yield of compound C was 3.28 g (30.6%). $^1$H NMR (C$_6$D$_6$): δ 7.21 (1H, d), 7.02 (2H, m), 2.47 (4H, q), 2.39 (1H, m), 1.11 (6H, t), 1.01 (6H, d).

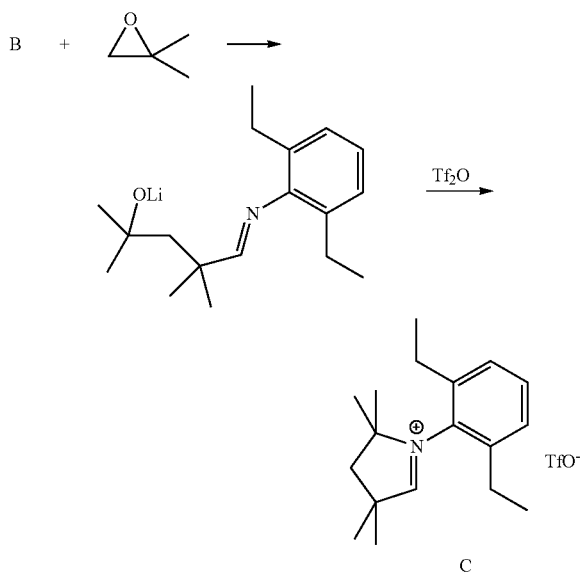

Example 1

Synthesis of 2-(2,6-diethylphenyl)-3,3,5,5-tetramethylpyrrolidine[2-(1-propoxy)-5-(N,N-dimethylaminosulfonyl)phenyl]methylene ruthenium dichloride (D), for comparison to Examples 2 and 3

Tetrahydrofuran (40 mL) was added to KN(SiMe$_3$)$_2$ (0.379 g, 1.90 mmol) to form a homogeneous solution. The solution was cooled to −80° C. and then a solution of C (0.775 g, 1.90 mmol) in THF (10 mL) was added dropwise over about 10 seconds. After 30 seconds, a solution of {[2-(i-propoxy)-5-(N,N-dimethylaminosulfonyl)phenyl]methylene}(tricyclohexylphosphine)ruthenium dichloride (0.612 g, 0.865 mmol) in THF (10 mL), which had been cooled to −10° C., was added dropwise over about 15 seconds. The mixture was stirred for 10 minutes then warmed to ambient temperature. The mixture was further stirred at ambient temperature for 2 hours and then the volatiles were removed under reduced pressure. The residue was extracted with 20 mL of a 3:2 mixture of hexane:CH$_2$Cl$_2$ and filtered. The filtrate was loaded on to a SiO$_2$ column (1.25"×8") that had been packed with the same solvent mixture. The column was eluted with 3:2 hexane:CH$_2$Cl$_2$ (300 mL) and then the solvent polarity was gradually increased to pure CH$_2$Cl$_2$. The product eluted as a dark green band. Removal of the volatiles afforded a dark green oil that crystallized upon the addition of pentane (2 mL) and cooling to −10° C. overnight. The product was isolated as green flocculent crystals (Compound D) that were dried under reduced pressure (0.038 g, 6.4%). $^1$H NMR (CD$_2$Cl$_2$): δ 16.26 (1H, s, RuCH—), 7.96 (1H, dd), 7.64 (1H, t), 7.47 (2H, d), 7.18 (1H, d, J=2 Hz), 7.11 (1H, d), 5.22 (1H, sept), 2.64 (6H, s), 2.53 (4H, m), 2.19 (2H, s), 2.07 (6H, s), 1.77 (6H, d), 1.32 (6H, s), 0.88 (6H, t).

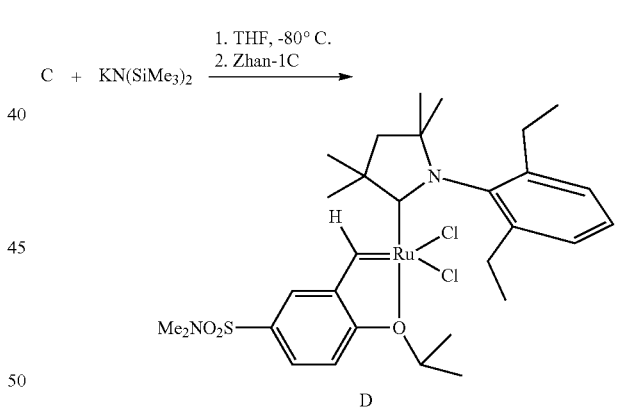

Examples 2 & 3

Synthesis of Compound 1, precursor to Compound D in Examples 2 and 3: Benzene (8 mL) was added to LiN(SiMe$_3$)$_2$ (0.163 g, 0.972 mmol) to form a clear colorless solution. Solid C (0.396 g, 0.972 mmol) was added in small portions to the stirring solution over a few minutes to give a yellow oily-looking mixture. After 15 minutes the mixture had become clear. After stirring for 1 hour the volatiles were removed under a stream of nitrogen to give a residue. The residue was extracted with pentane (8 mL) and filtered. Concentration of the solution to about 2 mL led to the formation of some crystalline solid. The solution was cooled to −10° C. overnight. The solids was isolated and dried under reduced pressure to yield Compound 1 as colorless crystals (0.341 g, 84.9%). $^1$H NMR (500 MHz, C$_6$D$_6$): δ 7.25 (1H, dd), 7.18 (2H, d), 2.66 (2H, pseudo sextet), 2.43 (2H, pseudo sextet), 1.50 (6H, s), 1.47 (2H, s), 1.34 (6H, t), 0.93 (6H, s). The molecular structure of Compound 1 was determined by single-crystal X-ray diffraction and is depicted in FIG. 1.

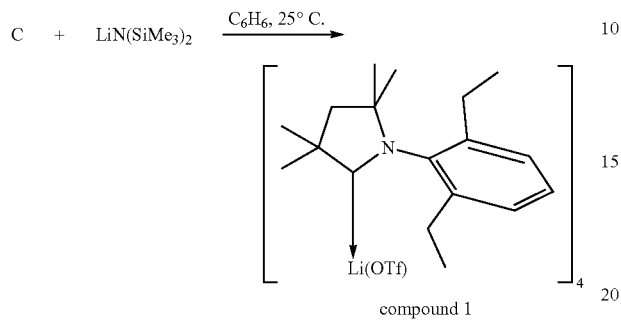

compound 1

Stability Studies of Compound 1 in Solution:

C$_6$D$_6$ solution: Compound 1 (ca. 10 mg) was combined with C$_6$D$_6$ (1 mL) to give a clear and colorless solution. $^1$H NMR spectroscopy indicated that the solution contained essentially pure (>95%) compound 1. After 4 days storage in the dark under an inert atmosphere $^1$H NMR spectroscopy indicated that only 14% of compound 1 had decomposed to unidentified products.

D$_8$-THF solution: Compound 1 (ca. 10 mg) was combined with D$_8$-THF (1 mL) to give a clear and colorless solution. $^1$H NMR spectroscopy indicated that the solution contained essentially pure (>95%) compound 1. After 17 hours storage in the dark under an inert atmosphere $^1$H NMR spectroscopy indicated that essentially none (<5%) of compound 1 had decomposed.

Example 2

Synthesis of D from Isolated Compound 1 and Zhan-1C.

Benzene (9 mL) was added to compound 1 (0.286 g, 0.692 mmol) and Zhan-1C (0.223 g, 0.315 mmol) to form a red-purple mixture that was then heated to 40° C. After 4 hours CuCl (0.312 g, 3.15 mmol) was added to the mixture. After 30 min the mixture was filtered, and the resulting green solution was loaded on a short silica gel column that had been packed with 1:1 CH$_2$Cl$_2$ and hexanes. The product was eluted as a green band using a 1:1 CH$_2$Cl$_2$-hexanes mixture and gradually increasing the solvent polarity to pure CH$_2$Cl$_2$. The green fraction was dried under reduced pressure to yield 0.192 g of compound D (89.0%) as a green solid which was. $^1$H NMR characterization is identical to that described above in Example 1.

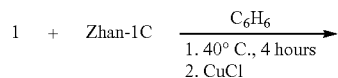

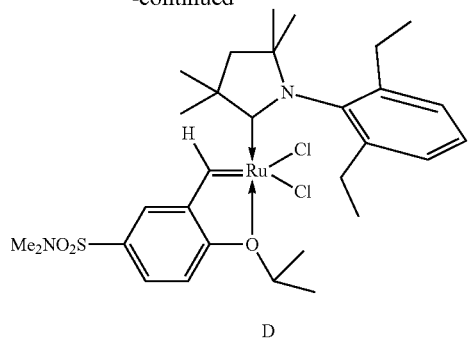

D

Example 3

Synthesis of D from In Situ Generated Compound 1 and Zhan-1C

Benzene (10 mL) was added to LiN(SiMe$_3$)$_2$ (0.185 g, 1.11 mmol) to form a clear colorless solution. Solid C (0.451 g, 1.11 mmol) was added in small portions to the stirring solution over a few minutes to give a yellow oily-looking mixture. After 30 minutes the mixture had become clear. Zhan-1C (0.314 g, 0.443 mmol) was then added and the mixture was heated to 40° C. After 4 hours, CuCl (0.438 g, 4.43 mmol) was added. After stirring for 30 min, $^1$H NMR analysis of an aliquot of the mixture indicated the presence of product 1 and Zhan-1C in a 95:5 ratio. The mixture was stirred for a further 20 minutes then filtered. The green solution was loaded on a short silica gel column (4 inches×1 inch) that had been packed with 1:1 CH$_2$Cl$_2$ and hexanes. The product was eluted as a green band using a 1:1 CH$_2$Cl$_2$-hexanes mixture and gradually increasing the solvent strength to pure CH$_2$Cl$_2$. The green fraction was dried under reduced pressure to yield compound D as a green solid (0.24 g, 79%). $^1$H NMR characterization is identical to that described above in Example 1.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications may be made without departing from the spirit and scope of the invention. Accordingly, it is not intended that the invention be limited thereby. Likewise, the term "comprising" is considered synonymous with the term "including" for purposes of Australian law.

What is claimed is:

1. A carbene complex of metal salt represented by the formula:

[T—M(R)$_c$]$_n$ wherein, R is selected from the group consisting of an alkyl sulfonate, aryl sulfonate, alkyl sulfate, aryl sulfate, carboxylate, aryl carboxylate, amidate, amidinate, thiocarboxylate, dithiocarboxylate, borate, chloride, bromide, iodide, nitrate, triflate, and perchlorate; c is 1 or 2; M is Li or Mg; n is an integer of from 1 to 24; and T is represented by Formula (I):

(Formula I)

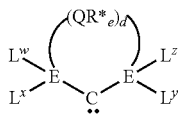

where e is 0, 1, or 2; d is 1, 2, 3, or 4; Q is C, Si, N, P, O, or S; each R* is a hydrogen, oxo, hydrocarbyl or substituted hydrocarbyl group; and each E is, independently, C, N, S, O, or P, with available valences, if any, occupied by $L^w$, $L^x$, $L^y$, and $L^z$, where $L^w$, $L^x$, $L^y$, and $L^z$ are, independently, hydrogen, hydrocarbyl groups or substituted hydrocarbyl groups, wherein the complex has 50% or less decomposition when stored in 0.01 molar benzene at 23° C. for a period of 1 hour.

2. The complex of claim 1, wherein $L^w$, $L^x$, $L^y$, and $L^z$ are independently selected from the group consisting of hydrocarbyl groups and substituted hydrocarbyl groups having 1 to 40 carbon atoms.

3. The complex of claim 1, wherein $L^w$, $L^x$, $L^y$, and $L^z$ are independently $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, aryl, and substituted aryl.

4. The complex of claim 1, wherein $L^w$, $L^x$, $L^y$, and $L_z$ are independently selected from the group comprising methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, tolulyl, chlorophenyl, 2,6-diethylphenyl, 2,6-diisopropylphenyl, 2-isopropylphenyl, 2-ethyl-6-methylphenyl, 3,5-ditertbutylphenyl, 2-tertbutylphenyl, and 2,3,4,5,6-pentamethylphenyl.

5. The complex of claim 1, wherein the complex has 40% or less decomposition when stored in 0.01 molar benzene at 30° C. for a period of 1 hour.

6. The complex of claim 1, wherein the complex has 10% or less decomposition when stored in 0.01 molar benzene at 30° C. for a period of 1 hour.

7. The complex of claim 1, wherein M is lithium.

8. The complex of claim 1, wherein the salt forms an oligomeric cluster.

9. The complex of claim 1, wherein n is 4 and the salt forms a cube-like oligomeric cluster in which M and R groups occupy the proximate vertices of the cube, as represented by:

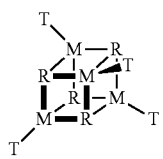

where M, R, and T are as defined in claim 1.

10. The complex of claim 9, wherein each M is Li, and each T is:

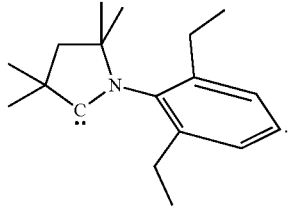

11. The complex of claim 1, wherein the salt forms a cube-like oligomeric cluster in which T is as defined in claim 1, each M is Li and each R is triflate, and the M and R groups occupy the proximate vertices of the cube, as represented by:

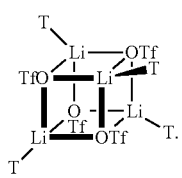

12. The complex of claim 1, wherein the complex is represented by the formula:

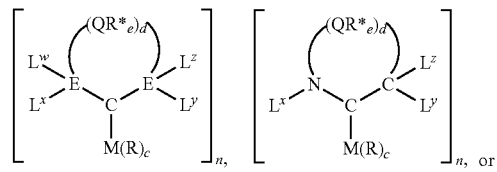

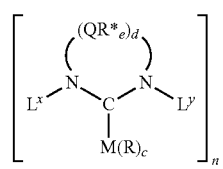

where n is 1, 2, 3, 4, 5, 6, 7, 8, 9, 10, 11, 12, 13, 14, 15, 16, 17, 18, 19, 20, 21, 22, 23, or 24; e is 0, 1, or 2; d is 1, 2, 3, or 4; Q is C, Si, N, P, O, or S; each R* is a hydrogen, oxo, hydrocarbyl or substituted hydrocarbyl group; and each E is, independently, C, N, S, O, or P, with available valences, if any, occupied by $L^w$, $L^x$, $L^y$, and $L^z$, where $L^w$, $L^x$, $L^y$, and $L^z$ are, independently, hydrogen, hydrocarbyl groups or substituted hydrocarbyl groups.

13. A transition-metal-carbene complex prepared using carbene complex of a lithium and/or magnesium salt, said transition-metal-carbene complex represented by the formula:

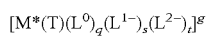

where M* is a transition metal from Group 6, 7, 8, 9, 10, 11, or 12; T is represented by Formula (I):

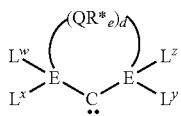
(Formula I)

where e is 0, 1, or 2; d is 1, 2, 3, or 4; Q is C, Si, N, P, O, or S; each R* is a hydrogen, oxo, hydrocarbyl or substituted hydrocarbyl group; and each E is, independently, C, N, S, O, or P, with available valences, if any, occupied by $L^w$, $L^x$, $L^y$, and $L^z$, where $L^w$, $L^x$, $L^y$, and $L^z$ are, independently, hydrogen, hydrocarbyl groups or substituted hydrocarbyl groups; $L^0$ is a neutral ligand; $L^{1-}$ is a monoanionic ligand; $L^{2-}$ is a dianionic ligand, where $L^0$, $L^{1-}$, and $L^{2-}$ are each selected from the group consisting of trialkylphosphines, pyridines, halides, alkyls, aryls, alkylidenes, ethers, and thio ethers; q is 0, 1, 2, 3, or 4; s is 0, 1, 2, 3, or 4; t is 0, 1, 2, 3, or 4; and g is the overall charge of the molecule.

14. A carbene complex of metal salt represented by the formula:

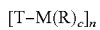

wherein, R is selected from the group consisting of an alkyl sulfonate, aryl sulfonate, alkyl sulfate, aryl sulfate, carboxylate, aryl carboxylate, amidate, amidinate, thiocarboxylate, dithiocarboxylate, borate, chloride, bromide, iodide, nitrate, triflate, and perchlorate; c is 1 or 2; M is Li or Mg; n is an integer of from 1 to 24; and T is represented by Formula (I):

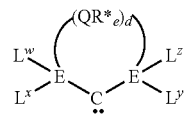
(Formula I)

where e is 0, 1, or 2; d is 1, 2, 3, or 4; Q is C, Si, N, P, O, or S; each R* is a hydrogen, oxo, hydrocarbyl or substituted hydrocarbyl group; and each E is, independently, C, N, S, O, or P, with available valences, if any, occupied by $L^w$, $L^x$, $L^y$, and $L^z$, where $L^w$, $L^x$, $L^y$, and $L^z$ are, independently, hydrogen, hydrocarbyl groups or substituted hydrocarbyl groups, wherein the complex has 50% or less decomposition when stored in 0.01 molar benzene at 23° C. for a period of 1 hour;

and wherein the salt forms a cube-like oligomeric cluster in which T is as defined in claim 1, each M is Li and each R is triflate, and the M and R groups occupy the proximate vertices of the cube, as represented by:

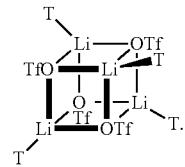

* * * * *